United States Patent [19]

Fitton et al.

[11] 4,208,334
[45] Jun. 17, 1980

[54] PROCESS FOR PREPARATION OF ALPHA-TOCOPHEROL

[75] Inventors: Peter Fitton, Pequannock; Ronald Propper, Fair Lawn, both of N.J.

[73] Assignee: Hoffmann-La Roche, Inc., Nutley, N.J.

[21] Appl. No.: 972,573

[22] Filed: Dec. 22, 1978

[51] Int. Cl.² .......................................... C07D 311/72
[52] U.S. Cl. ................................................... 260/345.5
[58] Field of Search ..................................... 260/345.5

[56] References Cited

U.S. PATENT DOCUMENTS

| 2,411,968 | 12/1946 | Karrer et al. | 260/345.5 |
| 2,723,278 | 11/1955 | Surmatis et al. | 260/345.5 |
| 3,789,086 | 1/1974 | Frick et al. | 260/345.5 |

OTHER PUBLICATIONS

Derwent No. 65663y, 1/28/76.
Derwent No. 65113y, 2/20/76.

*Primary Examiner*—Nicky Chan
*Attorney, Agent, or Firm*—Jon S. Saxe; Bernard S. Leon; William H. Epstein

[57] ABSTRACT

A process for producing α-tocopherol (Vitamin E) by condensing trimethylhydroquinone with either a phytol or an isophytol derivative thereof in the presence of trifluoroacetic acid.

9 Claims, No Drawings

PROCESS FOR PREPARATION OF α-TOCOPHEROL

BACKGROUND OF INVENTION AND STATEMENT OF PRIOR ART

In the past, 2,5,7,8-tetramethyl-2-(4,8,12-trimethyl-tridecyl)-6-chromanol (α-tocopherol) has been produced by condensing trimethylhydroquinone with a

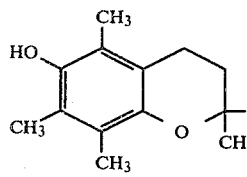

phytyl derivative. This condensation is generally carried out in the presence of a condensation agent such as a Lewis acid or a hydrohalic acid, (See U.S. Pat. Nos. 3,789,086; 2,723,278; and 2,411,968) at high temperatures, i.e. above 70° C. In these catalytic condensation reactions, the reaction mixture is generally kept saturated with anhydrous hydrogen chloride during the reaction. The anhydrous hydrogen chloride which is generated from concentrated hydrochloric acid is pumped through the reaction mixture and recondensed.

The above process suffers from the disadvantage that it must be carried out at very high temperatures. At very high temperatures, the use of these condensing agents and hydrogen chloride provides a very corrosive mixture. Furthermore, the use of high temperatures is by itself expensive and energy consuming.

In order to avoid the use of high temperatures, it has been found that by pretreating the isophytol with amine or ammonia such as disclosed in Derwent No. 65113Y or by utilizing a mixed ether-halohydrocarbon solvent mixture such as disclosed in Derwent No. 65663Y, lower tempertures can be utilized. However, none of these processes avoid the necessity of utilizing acid catalyts and anhydrous hydrogen chloride.

In utilizing hydrogen chloride, the spent hydrogen

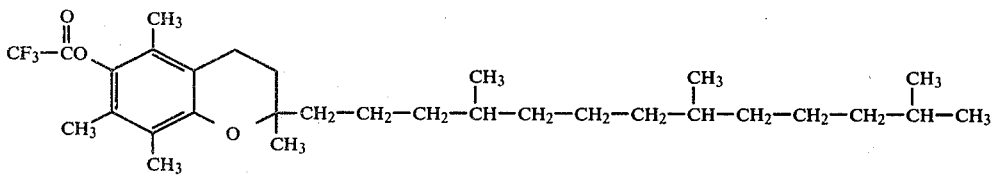

chloride is recycled after purification. In order to do this, a considerable amount of the equipment is required solely for processing hydrogen chloride. Also, another disadvantage of this process is that the quality of the alpha-tocopherol produced presents a purification problem. The impurities in alpha-tocopherol are difficult to remove since the crude alpha-tocopherol, under the conditions of fractional distillation, starts to decompose. Therefore, in order to purify the crude alpha-tocopherol, it must be converted to a alpha-tocopheryl acetate by reaction with acetic anhydride. The acetate which is fractionally distilled is hydrolyzed back to alpha-tocopherol. Even after this extensive purification, the purity of alpha-tocopherol is only between 90–96% with major losses in yield since many of the impurities are compounds that are closely related to alpha-tocopherol. In utilizing this procedure, it has been found that many of the impurities have the same molecular weight and almost the same boiling point as alpha-tocopherol and are thus practically impossible to remove by standard purification techniques.

SUMMARY OF THE INVENTION

In accordance with this invention, it has been discovered that α-tocopherol which has the formula:

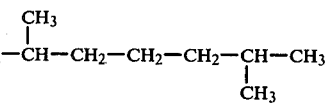

can be produced by reacting trimethyl hydroquinone which has the formula:

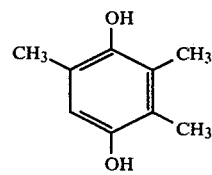

with a phytyl derivative of the formula:

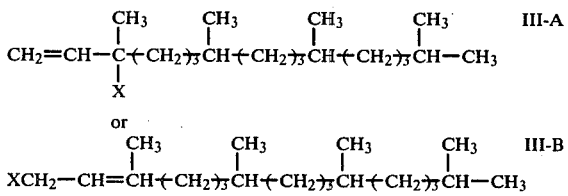

wherein X is a leaving group
in the presence of trifluoroacetic acid or trifluoroacetic acid anhydride. In this reaction, a compound of the formual:

can, if desired, be formed as an intermediate.

In accordance with this invention, it has been unexpectedly discovered that when a compound of formula II is reacted with a compound of formula III-A or III-B in the presence of trifluoro acetic acid, the compound of formula I is produced at low temperatures, i.e. room temperatures without the need for utilizing strong acids and/or Lewis acid condensing agents. This is extremely advantageous since condensation occurs at room temperature rather than at temperatures of 110° C., thereby reducing the energy costs and costs of using high temperature equipment. Furthermore there is no need to use Lewis acids such as zinc chloride or ferric chloride as catalysts in the condensation reaction thereby avoiding possible pollution problems. The elimination of the use of concentrated hydrochloride acid and the resulting anhydrous hydrogen chloride in the reaction provides considerable advantages. Besides substantially eliminating the corrosion problem, the need to generate anhydrous hydrogen chloride is also eliminated. Furthermore, in the process of this invention, there is no need to purify and recycle the hydrogen chloride.

It has also been found that the process of this invention produces alphatocopherol in higher yields and with higher purities than is obtained by the prior processes. In fact purities as high as 99.5 to 100% alpha-tocopherol are obtained due to the elimination of those impurities which have the same molecular weight and almost the same boiling point as alpha-tocopherol. By utilizing the claimed process, there is no need to convert the crude alpha-tocopherol to alpha-tocopherol acetate for purification, thereby eliminating a costly step utilized in prior processes.

DETAILED DESCRIPTION

As used throughout the specification, the term "halogen" includes all four halogens such as bromine, chlorine, fluorine and iodine, with bromine and chlorine being especially preferred.

The term "lower alkyl" includes saturated aliphatic hydrocarbon groups containing 1 to 7 carbon atoms such as methyl, ethyl, propyl, isopropyl, isobutyl, etc.

The term "lower alkoxy" includes lower alkoxy groups containing from 1 to 7 carbon atoms such as methoxy, ethoxy, n-butoxy, isobutoxy, etc.

The term "lower alkanoyl" includes lower alkanoyl groups containing from 1 to 7 carbon atoms, preferably from 2 to 7 carbon atoms such as acetyl, propionlyl, etc.

The term "aryl" as used herein denotes monocyclic aromatic hydrocarbons such as phenyl and polycyclic aromatic hydrocarbons such as naphthyl which may be unsubstituted or substituted in one or more positions with a lower alkyl or nitro group.

In accordance with this invention, the substituted X in the compounds of formula III-A and III-B can be any conventional leaving group. Among the preferred leaving groups are included hydroxy, halide, lower alkylsulfonyloxy, arylsulfonyloxy, lower alkoxy, and lower alkanoyloxy. Among the preferred halides are chlorine and bromine. Among the preferred lower alkylsulfonyloxy leaving groups are mexyloxy. The preferred arylsulfonyloxy leaving group is tosyloxy. The preferred lower alkanoyloxy group is acetoxy. Among the preferred lower alkoxy leaving groups are n-butoxy, methoxy, isobutoxy and ethoxy.

In accordance with this invention, the reaction of the compound of formula II with the compound of formula III-A or III-B is carried out in the presence of either trifluoroacetic acid or trifluoroacetic acid anhydride. In carrying out this reaction, good yeilds are obtained utilizing room temperature, i.e. temperatures of from 20° to 30° C. While it is generally preferred to carry out this reaction at room temperature, lower or higher temperatures can be utilized. In general, temperatures of from about 5° C. to about 70° C. are utilized.

The trifluoroacetic acid or trifluoroacetic acid anhydride can be utilized as the solvent medium. Therefore, it is not necessary to utilize additional solvents. However, if desired, other solvents can be utilized in the reaction medium. Among the other solvents which can be utlized include such conventional solvents as toluene, heptane, methylene chloride, acetic acid, diethyl either and aromatic hydrocarbon solvents such as benzene and xylene. The reaction of this invention can be carried out without the necessity of utilizing a Lewis acid, concentrated hydrochloric acid or other mineral acids. These materials may, if desired, be present, in the reaction medium. In view of the dilatorious effect of these materials, little if any advantage is seen in their use especially in the use of large quantities of mineral acids required by the prior art for carrying out this reaction.

In the reaction of a compound of formula III-A or III-B with a compound of the formula II to produce a compound of the formula I, the compound of the formula IV can, if desired, be formed as an intermediate. This intermediate is formed in a mixture with alpha-tocopherol. This intermediate in the reaction mixture can be converted directly to alpha-tocopherol by treating the reaction mixture with a base. Therefore, there is not need to isolate the compound of formula IV from the reaction medium. On the other hand, if desired, the compound of formula IV can be isolated in a mixture with the compound of formula I from the reaction medium. A compound of formula IV can be separated from the reaction medium by any conventional method of separation. Among the preferred methods of separating the compound of formula IV from the compound of formula I is by chromatography. Any conventional method of chromatography can be utilized to effect the separation.

The compound of formula IV can be converted to the compound of formula I by basic hydrolysis. Any conventional method of basis hydrolysis can be utilized to effect this conversion. Among the preferred methods is by treating the compound of formula V with an aqueous inorganic base. Among the aqueous bases are the strong bases such as alkali metal hydroxide such as sodium hydroxide, potassium hydroxide, lithium hydroxide. In carrying out this hydrolysis, it is generally preferred to utilize room temperature, i.e. from 20° to 30° C. However, if desired, higher or lower temperatures can be utilized, i.e. from 0° to 100° C.

The invention is further illustrated by the following examples. In the examples, the term "glc" denotes gas liquid chromotography.

EXAMPLE 1

Isophytol (98%, 255 g.) was added, dropwise, over a period of three hours to a vigorously stirred solution of trimethylhydroquinone (145.0 g.) in trifluoroacetic acid (750 ml.) at room temperature under nitrogen. When the addition was complete, the mixture was stirred for a further 30 minutes and then concentrated on a rotary evaporator (35° C./30 mmHg) to give an oil. This oil was dissolved in hexane (1 liter) and the solution was washed with methanol:water (1:1, v:v) (2 × 500 ml.) and 1N aqueous sodium bicarbonate solution (500 ml.). A 1% by weight solution of potassium hydroxide in methanol (200 ml.) was added and this mixture was stirred at room temperature for 30 minutes. Cold 10% by weight aqueous hydrochloric acid (200 ml.) was added. The organic layer was separated, washed with 1N aqueous sodium bicarbonate solution (500 ml.) and water (500 ml.), and then concentrated on a rotary evaporator (50° C./40 mm) to leave a brown oil (353.0 g.). This oil was flash-distilled and the following fractions were collected.

| Fraction | bp (°C.) | Pressure (mm) | wt. (g.) | Area % of α-tocopherol by glc |
|---|---|---|---|---|
| 1 | 137–234 | 0.05 | 12.3 | 47.6 |
| 2 | 234–259 | 0.05 | 9.1 | 91.0 |
| 3 | 259–278 | 0.05 | 312.1 | 99.7 |

EXAMPLE 2

Isophytol (98%, 25.5 g.) was added, dropwise, over three hours to a mixture of trimethylhydroquinone (14.5 g.), trifluoroacetic acid (65 ml.) and water (10 ml.). The product was diluted with hexane (200 ml.), washed with methanol-water (1:1, v:v)(3×100 ml.) and saturated aqueous sodium bicarbonate solution (100 ml.). A 1% by weight solution of potassium hydroxide in methanol (100 ml.) was added and the mixture was stirred at room temperature for 30 minutes. Then 2N aqueous hydrochloric acid (100 ml.) was added, the organic phase was separated, washed with saturated aqueous sodium bicarbonate solution (100 ml.) and methanol-water (1:1, v:v) (100 ml.). The hexane was removed by concentrating on a rotary evaporator and the resulting oil was flash-distilled to give α-tocopherol (29.6 g.; bp 220° C./0.1 mm.). Purity by area % glc was 100%.

EXAMPLE 3

Isophytol (98%, 25.5 g.) was added dropwise over a period of two hours to a mixture of trimethylhydroquinone (14.5 g.) in trifluoroacetic acid (150 ml.) at −5° C.

The resulting product was then refluxed for 22 hours under nitrogen, after which the excess trifluoroacetic acid was removed by concentration on a rotary evaporator (35° C./30 mmHg). The resulting oil was dissolved in hexane (100 ml.), the solution was washed with methanol-water (1:1, v:v) (3×100 ml.) and dried (Na₂SO₄). Removal of the hexane left an oil that on flash distillation (205°–215° C./0.2 mmHg) gave an oil (36.8 g.) which by glc analysis was shown to be a mixture of a α-tocopherol (6.7% by weight) and α-tocopheryl trifluoroacetate (88.5%).

The above mixture as the oil after removal of hexane was again diluted with hexane (200 ml.), washed with methanol-water (1:1, v:v) (3×100 ml.) and saturated aqueous sodium bicarbonate solution (100 ml.). A 1% by weight solution of potassium hydroxide in methanol (100 ml.) was added and the mixture was stirred at room temperature for 30 minutes. Then 2N aqueous hydrochloric acid (100 ml.) was added, the organic phase was separated, washed with saturated aqueous sodium bicarbonate solution (100 ml.) and methanol-water (1:1, v:v) (100 ml.). The hexane was removed by concentrating on a rotary evaporator and the resulting oil was flash-distilled to give α-tocopherol (bp 220° C./0.1 mmHg). Purity by area % glc was 100%.

EXAMPLE 4

Isophytol (98%, 255g, 0.84 moles) was added dropwise over a period of one hour to a vigorously stirred solution of trimethylhydroquinone (130.8g; 0.86 moles) in trifluoroacetic acid (750 ml) at room temperature under nitrogen. The mixture was stirred for a further 30 minutes and then concentrated on a rotary evaporator (35°–40° /30mmHg) to leave a brown oil. This oil was dissolved in hexane (1000ml) and the solution was washed with methanol: water (1:1 v:v) (2×500 ml) and 1N saturated aqueous sodium bicarbonate solution (500 ml), a 1% solution of potassium hydroxide in methanol (200 ml) was added and the mixture was stirred at room temperature for 30 minutes. Cold 10% aqueous hydrochloric acid (200 ml) was added, the organic layer was separated and washed with 1N aqueous bicarbonate solution (500 ml) and water (500 ml). concentration on a rotary evaporator leaving a brown oil (376.0 g). Glc analysis of this oil showed that it contained 88.5% by weight α-tocopherol (by use of an internal standard). This oil was flash distilled and the following fractions were collected:

| Fraction | bp (°C.) | Pressure (mm) | Wt (gm) | % Tocopherol by glc Area % | Wt % (internal standard) |
|---|---|---|---|---|---|
| 1 | 87–240 | 0.2 | 29.0 | 62.7 | |
| 2 | 240–246 | 0.2 | 12.43 | 99.4 | 99.0 |
| 3 | 246–260 | 0.12 | 289.91 | 99.9 | 99.9 |
| 4 | 260–280 | 0.12 | 12.99 | 99.8 | 89.9 |

What is claimed is:

1. A process for producing α-tocopherol comprising reacting a compound of the formula:

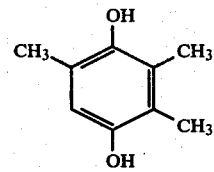

II with a phytyl derivative selected from the group consisting of

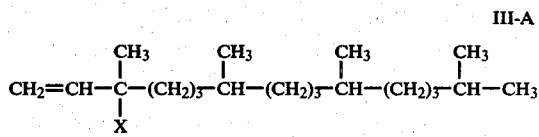

III-A and

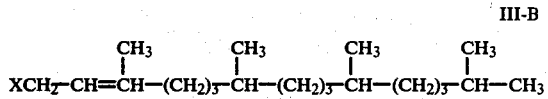

III-B wherein X is a leaving group in the presence of trifluoroacetic acid or trifluoroacetic acid anhydride.

2. The process of claim 1 wherein X is selected from the group consisting of arylsulfonyloxy, lower alkylsulfonyloxy, hydroxy, halogen, lower alkoxy and lower alkanoyloxy.

3. The process of claim 2 wherein X is hydroxy.

4. The process of claim 2 wherein X is lower alkylsulfonyloxy.

5. The process of claim 2 wherein X is tosyloxy.

6. The process of claim 2 wherein X is acetyloxy.

7. The process of claim 2 wherein X is tertiary butoxy.

8. The process of claim 1 wherein said phytyl derivative is iophytol.

9. The process of claim 8 wherein said reaction is carried out in trifluoroacetic acid.

* * * * *